US012559728B2

(12) United States Patent
Song et al.

(10) Patent No.: US 12,559,728 B2
(45) Date of Patent: Feb. 24, 2026

(54) LOW-SERUM MEDIUM COMPOSITION FOR CULTURING VERO CELLS AND USE THEREOF

(71) Applicant: LG CHEM, LTD., Seoul (KR)

(72) Inventors: Ji Hae Song, Daejeon (KR); Yang Hyun Kim, Daejeon (KR); Soojin Moon, Daejeon (KR); Min Jeong Kim, Daejeon (KR); Hye Suk Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 820 days.

(21) Appl. No.: 17/788,774

(22) PCT Filed: Dec. 24, 2020

(86) PCT No.: PCT/KR2020/019066
§ 371 (c)(1),
(2) Date: Jun. 24, 2022

(87) PCT Pub. No.: WO2021/133084
PCT Pub. Date: Jul. 1, 2021

(65) Prior Publication Data
US 2023/0036987 A1      Feb. 2, 2023

(30) Foreign Application Priority Data
Dec. 24, 2019      (KR) ........................ 10-2019-0174356

(51) Int. Cl.
*C12N 5/071* (2010.01)
*C12N 5/00* (2006.01)
*C12N 7/00* (2006.01)
*C12N 15/09* (2006.01)

(52) U.S. Cl.
CPC ......... *C12N 5/0686* (2013.01); *C12N 5/0075* (2013.01); *C12N 7/00* (2013.01); *C12N 15/09* (2013.01); *C12N 2500/95* (2013.01); *C12N 2501/33* (2013.01); *C12N 2760/00051* (2013.01)

(58) Field of Classification Search
None
See application file for complete search history.

(56) References Cited

U.S. PATENT DOCUMENTS

| 6,103,529 A | 8/2000 | Price et al. |
| 2004/0077086 A1 | 4/2004 | Reiter et al. |
| 2006/0094104 A1 | 5/2006 | Grillberger et al. |
| 2008/0227136 A1 | 9/2008 | Pla et al. |
| 2009/0246868 A1 | 10/2009 | Allikmets et al. |
| 2012/0077268 A1* | 3/2012 | Aerts et al. .............. C12N 5/02 |
| | | 435/349 |

FOREIGN PATENT DOCUMENTS

| CN | 101306199 A | 11/2008 |
| CN | 101474208 B | 9/2011 |
| CN | 101864393 B | 4/2012 |
| CN | 102805862 A | 12/2012 |
| CN | 102827804 A | 12/2012 |
| CN | 103160458 A | 6/2013 |
| CN | 108103007 A | 6/2018 |
| CN | 108853489 B | 7/2019 |
| CN | 110564672 A | 12/2019 |
| EP | 1983044 B1 | 8/2016 |
| JP | 5485863 B2 | 5/2014 |
| KR | 10-2007-0032273 A | 3/2007 |
| KR | 10-2007-0073930 A | 7/2007 |
| KR | 10-2014-0132017 A | 11/2014 |
| WO | 98-15614 A1 | 4/1998 |

OTHER PUBLICATIONS

El-Bagoury et al., "Optimizing culture conditions for increasing production of vero cell" Benha Vetinary Medical Journal (Year: 2019).*
Mattos et al. "Increasing Vero viable cell densities for yellow fever virus production in stirred tank bioreactors using serum-free medium" Vaccine (Year: 2015).*
Rourou et al., "Development of animal component free medium for vero cell cultures" Cell Culture and Tissue Engineering (Year: 2009).*
ThermoFisher Scientific Hyperforma 2:1 single use Bioreactor Brochure (Year: 2018).*
Feng et al., "Biotechnology Pharmaceuticals (For pharmaceutical professionals)," Jan. 31, 2016, China Medical Science and Technology Press, pp. 48-49.
Extended European Search Report dated Feb. 8, 2023, of the corresponding European Patent Application No. 20907923.5, 6 pages.
Clark, et al., "Serum Supplements and Serum-free Media: Applicability for Microcarrier Culture of Animal Cells" Developments in Biological Standardization, 1981, 50:81-91.
International Search Report issued for International Application No. PCT/KR2020/019066 on Apr. 8, 2021, 8 pages.
Chen et al., Applicability of modified M199 medium in Vero cell culture, Chinese Journal of Biologicals, 2014, 27, 1, pp. 76-77 (Abstract only, 1 page).
Kolell et al., Virus Production in Vero Cells Using a Serum-free Medium, Cell Technology for Cell Products, 2007, pp. 583-585.

* cited by examiner

*Primary Examiner* — Robert M Kelly
*Assistant Examiner* — John David Moore
(74) *Attorney, Agent, or Firm* — ROTHWELL, FIGG, ERNST & MANBECK, P.C.

(57) ABSTRACT

The present invention relates to a low-serum medium composition for culturing Vero cells, and a method for culturing Vero cells and a method for producing a virus, both using the same.

17 Claims, 9 Drawing Sheets

[FIG. 1]
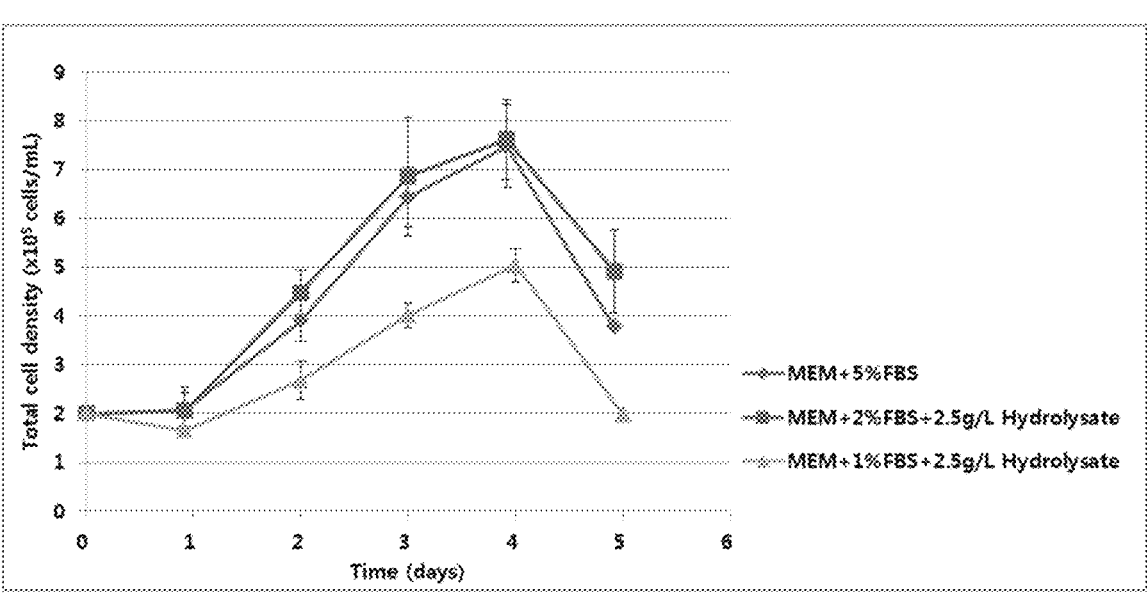

[FIG. 2]
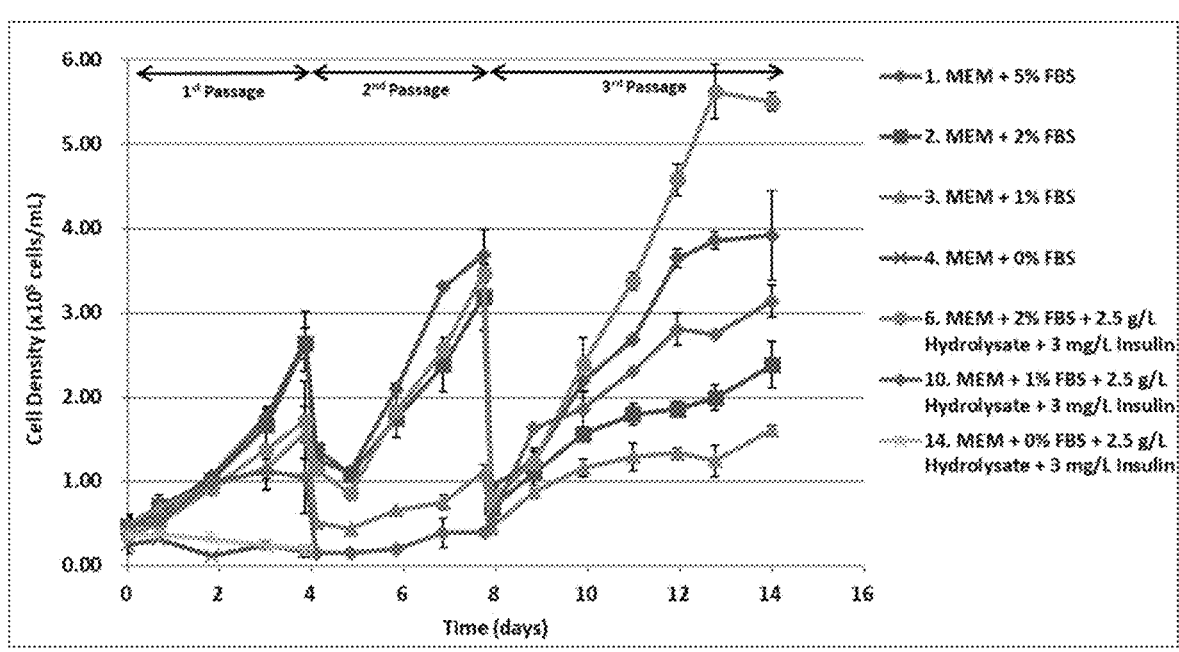

【FIG. 3】
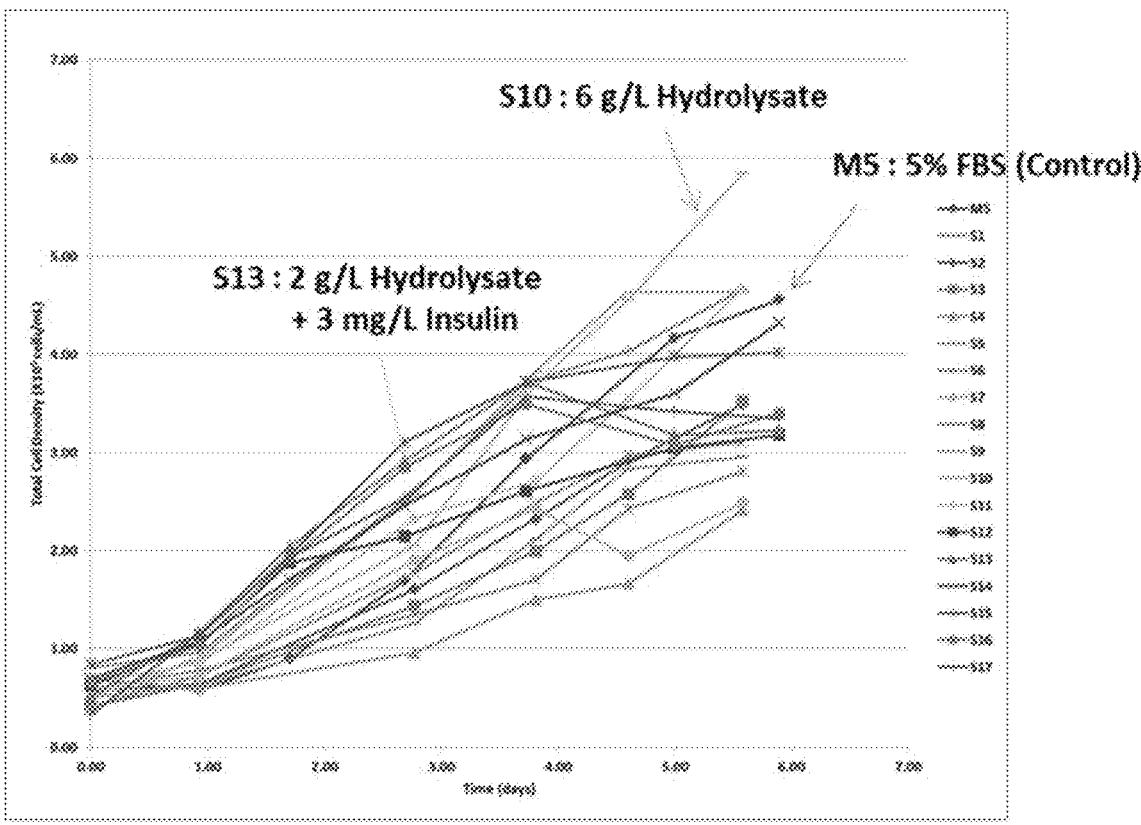
| FBS (%) | Hydrolysate (g/L) | Insulin (mg/L) | Sample ID |
|---------|-------------------|----------------|-----------|
| 1 | 0 | 0 | S1 |
| 1 | 0 | 6 | S2 |
| 1 | 6 | 0 | S3 |
| 1 | 6 | 6 | S4 |
| 1.5 | 3 | 3 | S5 |
| 1.5 | 3 | 3 | S6 |
| 1.5 | 3 | 3 | S7 |
| 2 | 0 | 0 | S8 |
| 2 | 0 | 6 | S9 |
| 2 | 6 | 0 | S10 |
| 2 | 6 | 6 | S11 |
| 2 | 2 | 0 | S12 |
| 2 | 2 | 3 | S13 |
| 2 | 2 | 6 | S14 |
| 2 | 4 | 0 | S15 |
| 2 | 4 | 3 | S16 |
| 2 | 4 | 6 | S17 |
| 5 | 0 | 0 | M5 |

【FIG. 4】
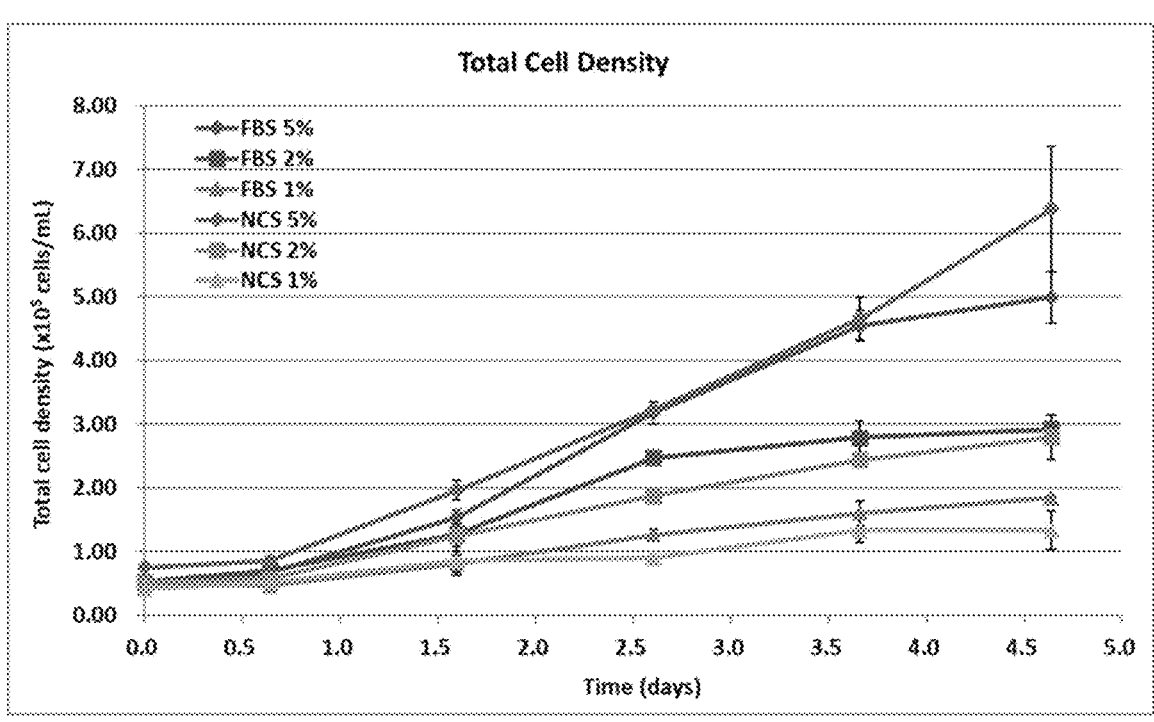

【FIG. 5】
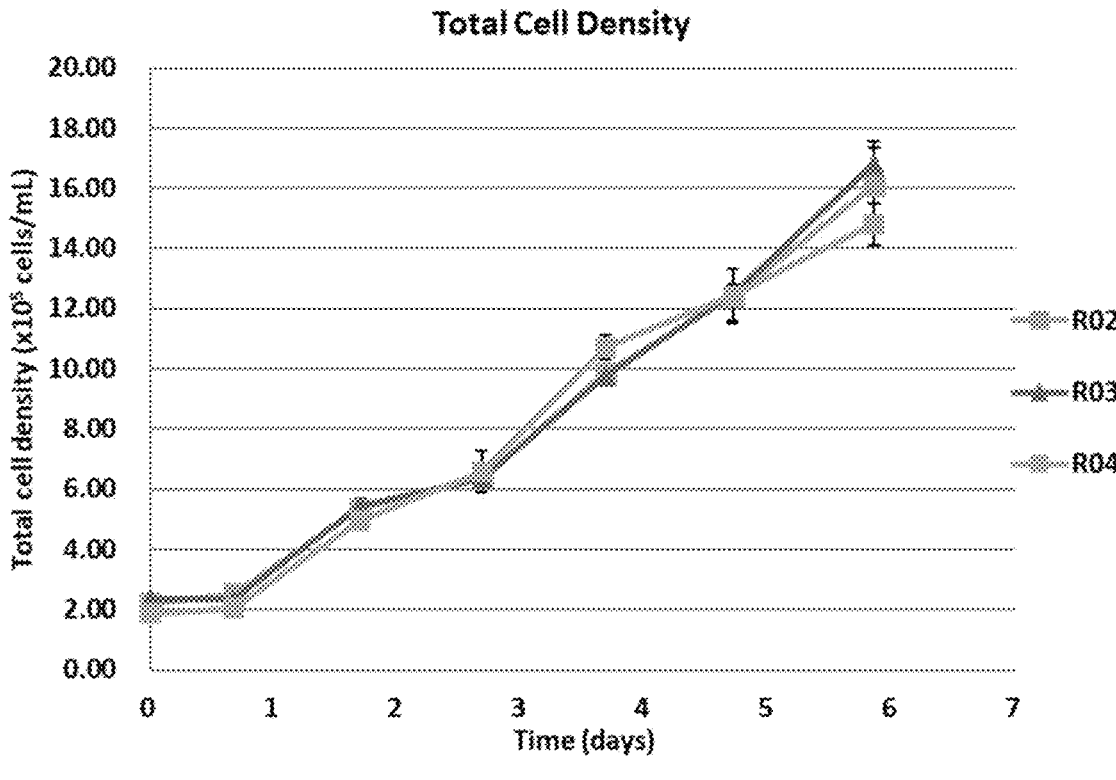
R02: MEM + 5% FBS
R03: MEM + 2%NCS + 2g/L Hydrolysate + 3mg/L Insulin
R04: MEM + 2% FBS + 2g/L Hydrolysate + 3mg/L Insulin R02: MEM+2%FBS + 2 g/L Hydrolysate + 3 mg/L Insulin
R03: MEM+7%NCS+2g/L Hydrolysate+3mg/L Insulin
R04: MEM+2% NCS+2g/L Hydrolysate+3mg/L Insulin

[FIG. 7]
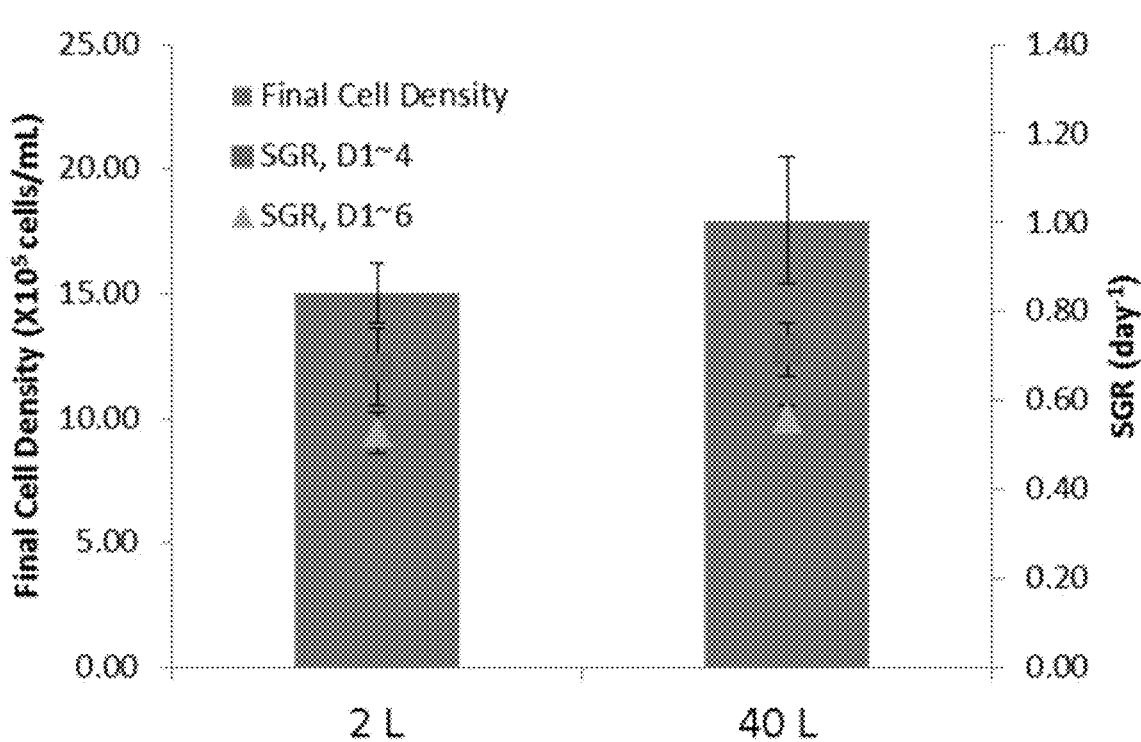
Cell Density & SGR (2 L vs. 40 L)

FIG. 8(a)
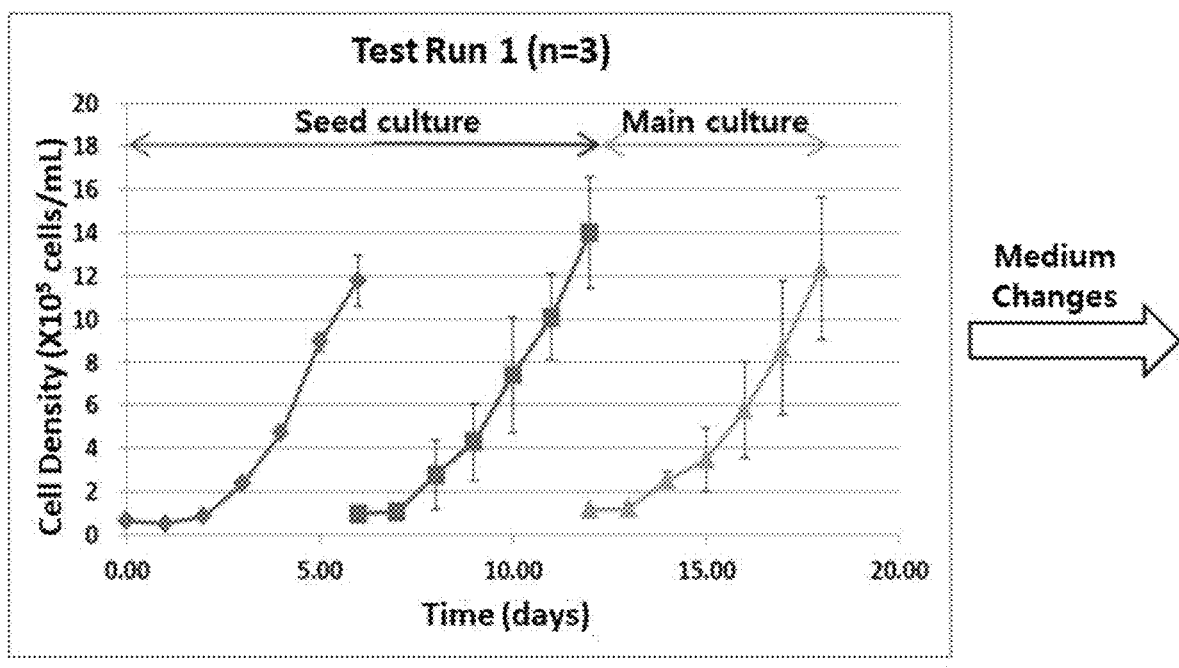
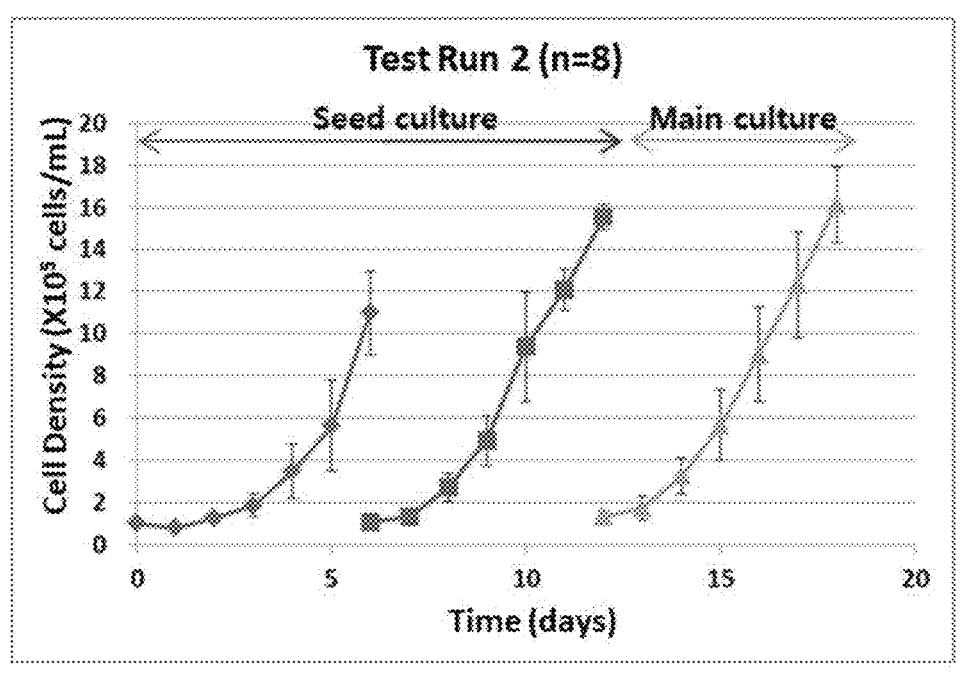

LOW-SERUM MEDIUM COMPOSITION FOR CULTURING VERO CELLS AND USE THEREOF

CROSS-REFERENCE TO RELATED APPLICATION

This application is a 35 U.S.C. 371 National Phase Entry Application from PCT/KR2020/019066 filed on Dec. 24, 2020, which claims priority from, Korean Patent Application No. 10-2019-0174356, filed on Dec. 24, 2019, the disclosures of which are hereby incorporated by reference herein in their entirety.

TECHNICAL FIELD

The present invention relates to low-serum medium composition for culturing Vero cells, and a method for culturing Vero cells and a method for producing a virus, both using the same.

BACKGROUND OF THE INVENTION

Vero cells are continuous cell lines that have been widely approved and used for the manufacture of viral vaccines. Vero cells were originally isolated from kidney cells extracted from an African green monkey and have been used to produce inactivated poliovirus vaccine (IPV), live oral poliovirus vaccine, rabies vaccine, etc. Vero cells have a broad range of susceptibility to various viruses, are reported to be safe against carcinogenesis, and do not pose a threat to human health according to the World Health Organization, and thus, Vero cell-based vaccines are now available worldwide.

In the conventional vaccine production using animal cells, it was common to use a medium to which an animal-derived material (e.g., serum, trypsin, albumin, etc.) is added in the step of proliferating the cells or infecting the cells with a virus to proliferate the virus. In particular, serum contains substances that promote the survival and proliferation of cells, such as nutrients, hormones, growth factors, and cytokines, plays an essential function in cell growth, protects cells from physical damage or shear forces, and facilitates adherent cells to adhere and spread on a vessel, and thus, it has the advantage of mimicking the culture medium similarly to the in vivo environment. However, due to the complexity of the chemical composition of serum, serum has disadvantages such as difficulty in producing a uniform product and thus providing various variables for cell growth, high unit price, a risk of infection with exogenous pathogenic agents for a vaccine produced using serum, and requiring a complicated downstream process.

Vero cells are adherent cells, which are generally cultured while attached to a microcarrier in a normal medium containing 10% fetal bovine serum (FBS). The major component contained in FBS is albumin, which is known to be a protein that plays an important role in cell adhesion. However, due to the disadvantages of the serum medium as described above, the need for a serum-reduced or serum-free medium is emerging.

BRIEF SUMMARY OF THE INVENTION

Technical Problem

Therefore, there is a demand for developing a medium having a composition containing supplements that can help cell adhesion and promote cell growth, instead of reducing the amount of serum in a medium.

Technical Solution

An embodiment described herein provides a medium composition for culturing Vero cells, including 1-7% (v/v) of newborn calf serum (NCS), 1-6 g/L of hydrolysate, and 1-6 mg/L of insulin.

Another embodiment described herein provides a method for culturing Vero cells, the method including culturing Vero cells in a medium composition including 1-7% (v/v) of newborn calf serum (NCS), 1-6 g/L of hydrolysate, and 1-6 mg/L of insulin.

Another embodiment described herein provides a method for producing a virus, the method including culturing Vero cells in a medium composition including 1-7% (v/v) of newborn calf serum (NCS), 1-6 g/L of hydrolysate, and 1-6 mg/L of insulin.

BRIEF DESCRIPTION OF DRAWINGS

FIG. 1 shows a result of Vero cell culture under the medium condition according to one embodiment described herein (Experiment No. 1).

FIG. 2 shows a result of Vero cell culture under the medium condition according to one embodiment described herein (Experiment No. 2).

FIG. 3 shows a result of Vero cell culture under the medium condition according to one embodiment described herein (Experiment No. 3).

FIG. 4 shows a result of Vero cell culture under the medium condition according to one embodiment described herein (Experiment No. 4).

FIG. 5 shows a result of Vero cell culture under the medium condition according to one embodiment described herein (Experiment No. 5).

FIG. 7 shows a result of Vero cell culture under the medium condition according to one embodiment described herein (Experiment No. 7).

DETAILED DESCRIPTION OF THE INVENTION

Figure 6A:
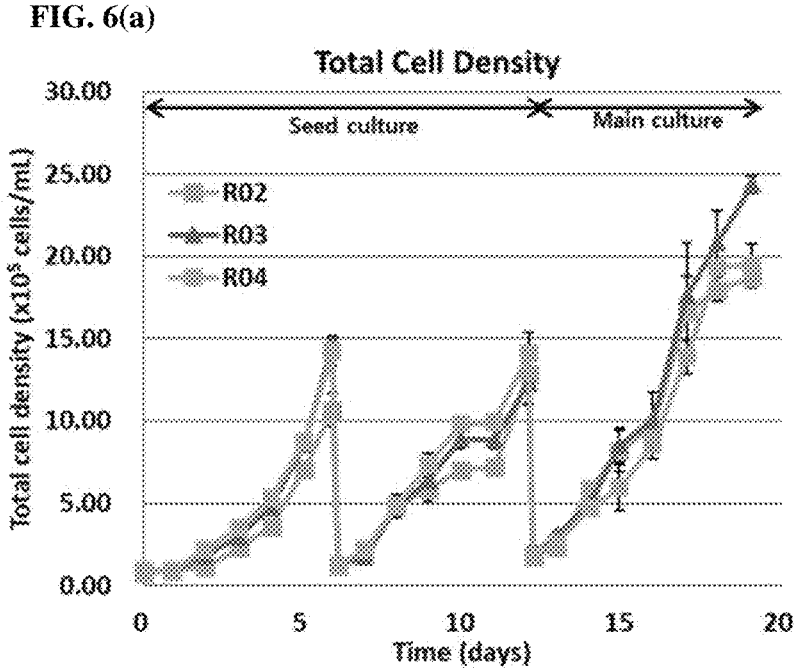
FIGS. 6(*a*) and 6(*b*) show a result of Vero cell culture under the medium condition according to one embodiment described herein (Experiment No. 6).

According to one aspect of the present invention, there is provided a medium composition for culturing Vero cells, including 1-7% (v/v) of newborn calf serum (NCS), 1-6 g/L of hydrolysate, and 1-6 mg/L of insulin.

In one embodiment, the medium composition may not contain fetal bovine serum (FBS).

In one embodiment, the hydrolysate may be an animal component-free and protein-free hydrolysate.

In one embodiment, Vero cells may be cultured while attached to a microcarrier in the medium composition.

In one embodiment, the medium composition may include culturing Vero cells attached to a microcarrier.

In one embodiment, the medium may include MEM medium.

According to another aspect of the present invention, there is provided a method for culturing Vero cells, including culturing Vero cells in the above-described medium composition.

In one embodiment, the culture may be implemented in a scale of 10 mL to 1000 L.

According to another aspect of the present invention, there is provided a method for producing a virus, the method including infecting Vero cells cultured in above described medium composition with a virus, and culturing the Vero cells infected with the virus.

In one embodiment, the culture of the Vero cells infected with the virus may be implemented in a scale of 10 mL to 2000 L.

Hereinafter, the present invention will be described in more detail.

The term "Vero cells" refers to any Vero cell line or cell line cultured or passaged therefrom, and includes, but is not limited to, genetically modified Vero cells. Non-limiting examples of known Vero cells may include VERO (ATCC Number CCL-81), VERO C1008 (ATCC Number CRL-1586), VERO 76 (ATCC Number CRL-1587), Vero-SF-ACF (ATCC Number CCL-81.5), etc.

The term "Vero cell culture" encompasses any procedure wherein Vero cells are grown or maintained in a viable state. For example, Vero cell culture includes not only procedures wherein the cells grow or proliferate but also procedures wherein the number of cells is not substantially increased but a viable state is maintained.

In a preferred example, the Vero cells described herein may be used as a substrate for a viral vaccine or virus- or viral vector-based therapy. In an embodiment, Vero cells may be infected with a virus to produce a virus. The virus that can be produced by the Vero cells may be an attenuated virus, a recombinant virus, or an oncolytic virus. The virus that can be produced by the Vero cells may be exemplified by, but is not limited to, poliovirus, enterovirus, infectious bursal disease virus (IBDV), rotavirus, measles virus, smallpox virus, influenza virus, Japanese encephalitis virus, rabies virus, Newcastle disease virus, respiratory syncytial virus (RSV), Sendai virus, simian virus 40 (SV40), chikungunya virus, and dengue virus.

The term "medium for culturing" refers to a composition that is used for culturing Vero cells and contains components necessary for growth. The medium for Vero cells described herein may be based on any medium generally known in the art such as MEM, DMEM, DMEM/F12, MDSS2, CCM5, Medium 199, MEM, or RPMI.

Such culture medium may include a number of components including amino acids, vitamins, organic and inorganic salts, and sources of carbohydrate, that support the cultivation of Vero cells.

As described herein, "comprising (the specified components)" may mean that it may include additional components other than the listed components ("comprising"), or it may essentially include the listed components ("consisting essentially of").

In a preferred example, a medium for culturing Vero cells described herein refers to a medium in which a basal medium is supplemented with 1-7% (v/v) of newborn calf serum (NCS), 1-6 g/L of hydrolysate, and 1-6 mg/L of insulin.

In another example, a medium for culturing Vero cells described herein refers to a medium in which a basal medium is supplemented with 1-7% (v/v), for example, 1-7% (v/v), 1-6% (v/v), 1-5% (v/v), 1-4% (v/v), 1-3% (v/v), 1% (v/v), 2% (v/v), 3% (v/v), 4% (v/v), 5% (v/v), 6% (v/v), or 7% (v/v) of newborn calf serum (NCS); 1-6 g/L, for example, 1-6 g/L, 1-5 g/L, 1-4 g/L, 1-3 g/L, 1-2 g/L, 2-4 g/L, 2-3 g/L, or 2 g/L of hydrolysate; and 1-6 mg/L, for example, 1-6 mg/L, 1-5 mg/L, 1-4 mg/L, 1-3 mg/L, 2-6 mg/L, 2-5 mg/L, 2-4 mg/L, 2-3 mg/L, or 3 mg/L of insulin.

Newborn calf serum (NCS) refers to serum from newborn calves, which is collected from calves typically of about 20 days old or younger, for example, about 14 days old or younger, about 10 days old or younger, or about 3 to 10 days old, and is sold at 1/10 the price of fetal bovine serum (FBS). As it is essential to secure the price competitiveness for a newly developed vaccine to enter the bidding market, the use of newborn calf serum (NCS) instead of fetal bovine serum (FBS) has a clear cost reduction effect. In addition, newborn calf serum (NCS) has a more stable supply and less lot-to-lot variation than fetal bovine serum (FBS), which makes it possible to obtain consistent experimental results, as well as is advantageous from an animal ethics point of view.

In the medium composition described herein, 1-7% (v/v) of newborn calf serum (NCS) is available, which is a lower concentration than FBS concentration condition commonly used for Vero cell culture, 10% FBS.

As the medium composition described herein contains 1-7% (v/v) of newborn calf serum (NCS), NCS is available at a lower concentration than FBS concentration condition commonly used for Vero cell culture, 10% FBS.

According to the examples described herein, cell growth is promoted under 1-7% (v/v) NCS conditions, and virus productivity shows similar results within the above range. Thus, for example, 1-7% (v/v), 1-6% (v/v), 1-5% (v/v), 1-4% (v/v), or 1-3% (v/v), more specifically 1-3% (v/v) or 2% (v/v), etc., may be suggested as preferred concentrations. However, the concentration range may be suitably increased or decreased within the ordinary skill of a person skilled in the art when other culture conditions affecting virus productivity are changed.

A "hydrolysate" described herein refers to a substance obtained by the hydrolysis of a peptide bond of a protein, which may be derived from milk (e.g., casein, whey protein), animal (e.g., meat, collagen), or plant. For example, the vegetable hydrolysate may be, but is not limited to, soy hydrolysate, wheat hydrolysate, potato hydrolysate, cottonseed hydrolysate, rice hydrolysate, pea hydrolysate, corn hydrolysate, and the like.

In one preferred example, in order to reduce lot-to-lot variation of hydrolysate and to efficiently carry out the downstream process, animal component-free and protein-free hydrolysate, which is produced by modifying methods of digestion, processing, etc., may be used herein. Examples of commercially available animal component-free and protein-free hydrolysate include, but are not limited to, Hypep™ 1510, Hypep™ 1511, Hypep™ 5603, Sheff-CHO PF ACF, Sheff-CHO Plus PF ACF, Sheff-VAX PF ACF SheffVax Plus PF ACF, SheffVax Plus PF ACF V, etc.

Although the medium composition described herein may contain 1-10 g/L of hydrolysate, as the cell growth could be negatively affected by a high concentration condition, the examples described herein limited the concentration up to 6 g/L to carry out experiments. Therefore, in one preferred example, considering the concentration that positively affects the cell growth, 1-6 g/L, for example, 1-6 g/L, 1-5 g/L, 1-4 g/L, 1-3 g/L, 1-2 g/L, 2-4 g/L, 2-3 g/L, or 2 g/L of hydrolysate, may be suggested as preferred concentrations. However, the concentration range may be suitably increased or decreased within the ordinary skill of a person skilled in the art when other culture conditions affecting virus productivity are changed.

The medium composition described herein also contains insulin. For example, the insulin may be natural insulin or recombinant insulin, and more specifically, human recombinant insulin, but is not limited thereto.

In the medium composition described herein, 1-6 mg/L, 1-5 mg/L, 1-4 mg/L, 1-3 mg/L, 2-6 mg/L, 2-5 mg/L, 2-4 mg/L, 2-3 mg/L, or 3 mg/L of insulin may be contained. However, the concentration range may be suitably increased or decreased within the ordinary skill of a person skilled in the art when other culture conditions affecting virus productivity are changed.

In one preferred example, Vero cells may be cultured while attached to a carrier such as a microcarrier. A microcarrier refers to any solid support matrix having a microlevel diameter and to which Vero cells can be attached. For example, cells can be attached to the surface thereof and cultured in a suspended state in a liquid medium. Examples of the material of the microcarrier include, but are not limited to, plastics such as polystyrene, polyethylene, polypropylene, polyester, polycarbonate, polyamide, polyacetal, and polyurethane, and copolymers thereof; glass; ceramic; metal; acrylamide; silica; silicone rubber; polylysine; cellulose; dextran; collagen (gelatin); and glycosaminoglycans, etc. A microcarrier may have a diameter of at least about 100 μm, at least about 200 μm, at least about 300 μm, at least about 400 μm, at least about 500 μm, at least about 600 μm, at least about 700 μm, at least about 800 μm, at least about 900 μm, or at least about 1 mm, and may have any shape such as bead (spherical), disk, strip, sheet, fiber, filament, rod, disk, cube, tube, but is not limited thereto. In one embodiment, a microcarrier may be porous.

In one preferred example, the culture of Vero cells may be implemented in a scale of 10 mL to 1000 L or more, for example, 10 mL to 2000 L or more, and Vero cells can be produced on a scale of 10 mL or more in a bioreactor. A "bioreactor" refers to any vessel that can be used for culturing Vero cells, and includes a fixed-bed bioreactor that is a bioreactor having a fixed bed including microcarriers. Vero cells herein may be cultured on a microcarrier in a bioreactor, or in another example, may be cultured in suspension in a bioreactor either in a batch process or in a fed-batch process.

During the culturing process of Vero cells, the medium may be exchanged as needed during the culture period. The pH of the medium is preferably about 6 to 8, or may be about 6.5 to 7.5, or about 7. Cultivation may be carried out for about 5 to 9 days at about 35° C. to 40° C., and aeration or agitation may be added as necessary, but is not limited thereto. The dissolved oxygen (DO) during cell culture may be about 60 to 90%, about 70 to 80%, etc., but is not limited thereto.

The Vero cells cultured according to the present invention may be used to produce a virus as a substrate for a viral vaccine or virus- or viral vector-based therapy. In this regard, the present invention also provides a method for producing a virus, including infecting Vero cells cultured in the medium composition as described above with a virus, and culturing the Vero cells infected with the virus.

Virus-infected Vero cells may be cultured under optimized conditions for propagating viruses. For example, the Vero cells may be cultured at a first temperature before infection with the virus and at a second temperature after infection with the virus, wherein the second temperature is lower than the first temperature. For example, the Vero cells may be cultured at about 37° C. before infection with the virus, i.e., pre-infection, and from about 29° C. to about 37° C. after infection with the virus, i.e., post-infection. In another example, the Vero cells may be cultured at about 33° C. after infection with the virus. In another example, the Vero cells may be cultured at about 30° C. after infection with the virus. The point of infection may be 1 day, 2 days, or 3 or 4 days after cell-seeding.

Following the completion of virus cultivation, the microcarrier may be removed and the virus fluid containing the virus may be recovered. The resulting virus fluid may be filtered using a filter membrane or the like to remove cell debris, or may be concentrated and/or purified before or after inactivation. Examples of methods of concentration may include ultrafiltration, ultracentrifugation, dialysis, etc., and examples of the methods of purification include, but are not limited to, methods which utilize physical characteristics of the substance being purified, such as size, density, and sedimentation coefficient, and methods which utilize chemical or physicochemical reactions (e.g., adsorption-desorption).

Hereinafter, the present invention will be described in more detail with reference to the following examples. However, these examples are only for illustrating the present invention, and the scope of the present invention is not limited by these examples.

Confirmation of Optimal Medium Composition for Vero Cells

The following experiment was designed to find the optimal medium composition for Vero cells. Vero cells were attached to microcarriers and cultured in shake flasks or bioreactors.

TABLE 1

| Experiment No. | Control Group | Experimental Group | Experiment Scale |
|---|---|---|---|
| 1 | 5% FBS | 2% FBS + 2.5 g/L hydrolysate 1% FBS + 2.5 g/L hydrolysate | 40 mL (shake flasks) |
| 2 | 5% FBS | 2% FBS 1% FBS 0% FBS 2% FBS + 2.5 g/L hydrolysate + 3 mg/L insulin 1% FBS + 2.5 g/L hydrolysate + 3 mg/L insulin 0% FBS + 2.5 g/L hydrolysate + 3 mg/L insulin | 30 mL (shake flasks) |
| 3 | 5% FBS | 1-2% FBS + 0-6 g/L hydrolysate + 0-6 mg/L insulin | 30 mL (shake flasks) |
| 4 | 5% FBS | 1%, 2% FBS 1%, 2%, 5% NCS | 30 mL (shake flasks) |
| 5 | 5% FBS | 2% FBS + 2 g/L hydrolysate + 3 mg/L insulin 2% NCS + 2 g/L hydrolysate + 3 mg/L insulin | 2 L (BRX) |
| 6 | 2% FBS + 2 g/L hydrolysate + 3 mg/L insulin | 2% NCS + 2 g/L hydrolysate + 3 mg/L insulin 7% NCS + 2 g/L hydrolysate + 3 mg/L insulin | 2 L (BRX) |
| 7 | 2 L | 40 L 1000 L | 40 L 1000 L |

Materials

Hydrolysate (Kerry, Ireland)

Insulin: Recombinant Human Insulin (Gibco, USA)

FBS: Fetal Bovine Serum (Hyclone, USA)

NCS: Newborn Calf Serum (Hyclone, USA)

BRX: Bioreactor (Model: Biostat B, Sartorius, Germany)

Experiment No. 1.

The effect of FBS concentration reduction and hydrolysate addition on Vero cell growth was evaluated. Vero cells were derived from ATCC Number CCL-81. As a control group, a MEM medium containing amino acids, vitamins, minerals, glucose, etc., supplemented with 5% FBS was used, and as an experimental group, MEM media each supplemented with 2% FBS+2.5 g/L hydrolysate, or 1% FBS+2.5 g/L hydrolysate, were used. As a result of culturing the prepared Vero cells in 40 mL of the prepared medium for 5 days (incubated at 37° C., 5% $CO_2$, 80±5% humidity), while the cell growth profile was similar in the medium supplemented with 2% FBS+2.5 g/L hydrolysate, and in the control group, the cell growth was decreased in the medium supplemented with 1 FBS+2.5 g/L hydrolysate compared to the control group (FIG. 1).

Experiment No. 2.

The effect of reduction of FBS concentration and addition of hydrolysate and insulin on Vero cell growth was evaluated. Vero cells were derived from ATCC Number CCL-81. As a control group, a MEM medium containing amino acids, vitamins, minerals, glucose, etc., supplemented with 5% FBS was used, and as an experimental group, MEM media each supplemented with 2% FBS, 1% FBS, 0% FBS, 2% FBS+2.5 g/L hydrolysate+3 mg/L insulin, 1% FBS+2.5 g/L hydrolysate+3 mg/L insulin, or 0% FBS+2.5 g/L hydrolysate+3 mg/L insulin were used. As a result of passaging the prepared Vero cells 3 times in 30 mL of the prepared medium for 14 days (incubated at 37° C., 5% $CO_2$, 80±5% humidity), the cell growth profile was higher in the medium supplemented with 2% FBS+2.5 g/L hydrolysate+3 mg/L insulin than in the control group. In the medium supplemented with 1 FBS+2.5 g/L hydrolysate+3 mg/L insulin, the cell growth was decreased compared to the control group, but the growth profile was higher than in the medium supplemented with 2% FBS group, and thus, the distinct growth promoting effect due to the hydrolysate and insulin was confirmed. In the medium without FBS, the cells were not grown even after adding hydrolysate and insulin, and thus, the culture was stopped at the 1st passage (FIG. 2).

Experiment No. 3.

The optimal concentrations of hydrolysate and insulin were evaluated. Vero cells were derived from ATCC Number CCL-81. As shown in the following table, as a control group, a MEM medium supplemented with 5% FBS was used, and as an experimental group, MEM media each supplemented with 0-6 g/L hydrolysate+0-6 mg/L insulin were used.

TABLE 2

| Sample ID | FBS (%) | Hydrolysate (g/L) | Insulin (mg/L) |
|---|---|---|---|
| M5 | 5 | 0 | 0 |
| S1 | 1 | 0 | 0 |
| S2 | 1 | 0 | 6 |
| S3 | 1 | 6 | 0 |
| S4 | 1 | 6 | 6 |
| S5 | 1.5 | 3 | 3 |
| S6 | 1.5 | 3 | 3 |
| S7 | 1.5 | 3 | 3 |
| S8 | 2 | 0 | 0 |

TABLE 2-continued

| Sample ID | FBS (%) | Hydrolysate (g/L) | Insulin (mg/L) |
|---|---|---|---|
| S9 | 2 | 0 | 6 |
| S10 | 2 | 6 | 0 |
| S11 | 2 | 6 | 6 |
| S12 | 2 | 2 | 0 |
| S13 | 2 | 2 | 3 |
| S14 | 2 | 2 | 6 |
| S15 | 2 | 4 | 0 |
| S16 | 2 | 4 | 3 |
| S17 | 2 | 4 | 6 |

As a result of culturing the prepared Vero cells in 30 mL of the prepared medium for 6 days (incubated at 37° C., 5% $CO_2$, 80±5% humidity), although the final cell number was the highest under the condition of 6 g/L hydrolysate (S10), under the condition of 2 g/L hydrolysate, the condition of supplementing with 3 mg/L insulin (S13) was selected as the condition for culturing in the bioreactor. As the results showed that the cell growth rate was fast in the early stage of culture, fed-batch culture in a bioreactor was considered a more favorable condition for cell growth (FIG. 3).

Experiment No. 4.

It was determined whether FBS can be replaced with NCS at different concentrations. Vero cells were derived from ATCC Number CCL-81. As a control group, a MEM medium supplemented with 5% FBS was used, and as an experimental group, MEM media each supplemented with 2% FBS, 1%, 2%, or 5% NCS were used. As a result of culturing the prepared Vero cells in 30 mL of the prepared medium for 5 days (incubated at 37° C., 5% $CO_2$, 80±5% humidity), similar cell growth profiles were observed when FBS and NCS were present at the same concentration, respectively (FIG. 4), suggesting that FBS can be replaced with NCS.

Experiment No. 5.

The experiment was conducted by expanding the conditions selected in Experiment No. 3 to the scale of a 2 L incubator, and it was determined whether FBS can be replaced with NCS by adding the condition of 2% NCS+2 g/L hydrolysate+3 mg/L insulin. Vero cells were derived from ATCC Number CCL-81. As a control group, a MEM medium supplemented with 5% FBS (#R02) was used to perform seed culture and main culture, and as an experimental group, MEM media each supplemented with 2% NCS+2 g/L hydrolysate+3 mg/L insulin (#R03) or 2% FBS+2 g/L hydrolysate+3 mg/L insulin (#R04) were used to perform seed culture and main culture (Temperature 37° C., pH 7.2±0.05, DO 50%, Culture method: Fed-batch, Culture days: Seed culture and main culture for 18 days).

As a result, similar cell growth profiles were shown when conditions of the MEM medium supplemented with 5% FBS, the medium supplemented with 2% FBS+2 g/L hydrolysate+3 mg/L insulin, and the medium supplemented with 2% NCS+2 g/L hydrolysate+3 mg/L insulin were used (FIG. 5), suggesting that a composition of 5% FBS can be replaced with a composition supplemented with 2% FBS or NCS, hydrolysate, and insulin, and FBS can be replaced with NCS.

Experiment No. 6.

Figure 6B:
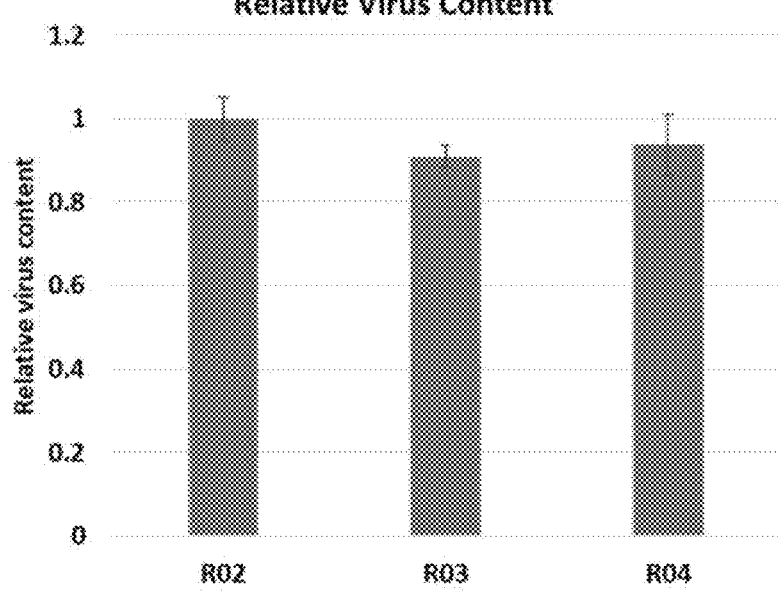

In the Experiment No. 6, it was intended to confirm the effect on cell growth and virus productivity depending on the concentration of NCS in the composition including hydrolysate and insulin. Vero cells were derived from ATCC Number CCL-81. As a control group, a MEM medium supplemented with 2% FBS+2 g/L hydrolysate+3 mg/L insulin was used (#R02), and as an experimental group, a MEM medium supplemented with 2% NCS+2 g/L hydrolysate+3 mg/L insulin (#R04) or a MEM medium supplemented with 7% NCS+2 g/L hydrolysate+3 mg/L insulin (#R03) were used. As a result of culturing the prepared Vero cells in a 2 L bioreactor for 19 days (Temperature 37° C., pH 7.2±0.05, DO 50%, Culture method: Fed-batch, Culture days: Seed culture and main culture for 19 days), the cell growth profile in the MEM medium supplemented with 2% NCS+2 g/L hydrolysate+3 mg/L insulin was found to be similar to that of the control group, suggesting that FBS can be replaced with NCS. Further, it was found that the cell growth was increased in the condition of 7% NCS concentration compared to the condition of 2% NCS (FIG. 6). Cells cultured under each condition were infected with the virus, recovered after 4 days of incubation (at temperature of 32.5° C., pH 7.4±0.1, DO 25%, Culture days: 4 days), and the virus concentration was quantified to compare productivity. Although the condition of 7% NCS+2 g/L hydrolysate+3 mg/L insulin (#R03) showed the highest final cell number, it showed similar virus productivity when compared to the condition 2% NCS+2 g/L hydrolysate+3 mg/L insulin (#R04). Therefore, it was confirmed that FBS can be replaced with NCS based on the Vero cell culture growth, and the virus productivity using virus culture. Thus, a composition of 2% NCS+2 g/L hydrolysate+3 mg/L insulin was selected to conduct the experiment for expanding the culture scale (FIG. 6).

Experiment No. 7.

It was determined whether cell growth is maintained by expanding the culture scale to 2 L, 40 L, and 1000 L with a medium composition including NCS, hydrolysate, and insulin (2% NCS+2 g/L hydrolysate+3 mg/L insulin), which were selected to replace FBS through the previous experiments culture (Temperature 37° C., pH 7.2±0.05, DO 50%, Culture method: Fed-batch, Culture days: Seed culture and main culture for 18 days). Vero cells cultured under each condition were infected with the virus, and recovered after 3-4 days of incubation to compare virus productivity. The results of comparing cell growth in the 2 L and 40 L culture scales are shown in the table below and FIG. 7, wherein the equal or higher cell growth results were confirmed even at the 40 L scale.

TABLE 3

| Culture Scale | 2 L (n = 6) | 40 L (n = 3) |
|---|---|---|
| final cell density (×10⁵ cells/mL) | 15.03 | 17.95 |
| SGR, D 1-4 (day⁻¹) | 0.68 | 0.71 |
| SGR, D 1-6 (day⁻¹) | 0.53 | 0.56 |

* SGR: specific growth rate

Figure 8B:
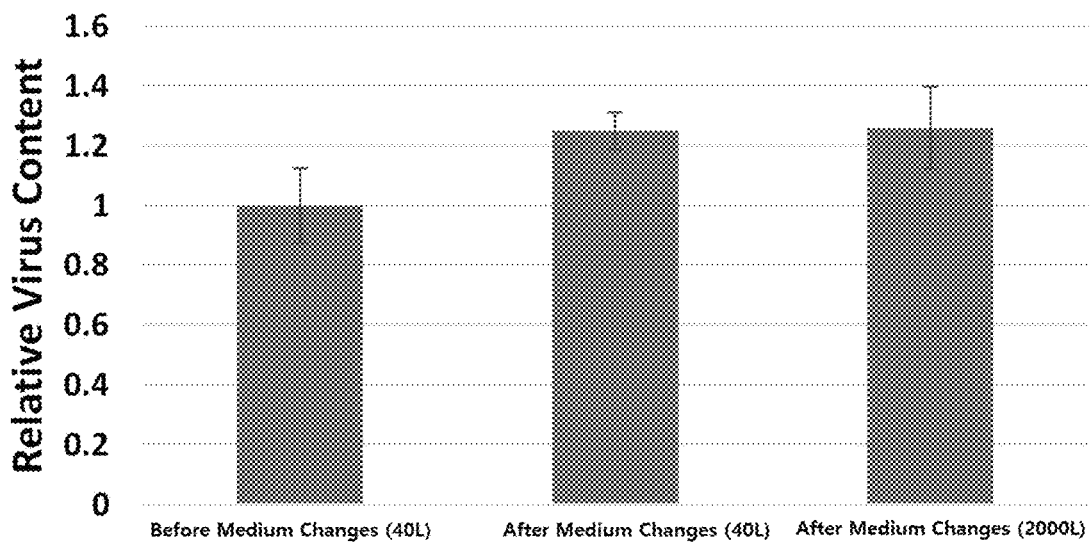
FIGS. 8(*a*) and 8(*b*) show results of Vero cell culture under the medium conditions, in a scale of 2 L and 40 L for FIG. 8 (*a*) and 1000 L for FIG. 8(*b*) according to one embodiment described herein (Experiment No. 7).

In addition, the results of comparing cell growth under the conditions of the medium containing FBS and the medium containing NCS, hydrolysate, and insulin in the 1000 L scale are shown in FIG. 8, wherein the equal or higher cell growth results were confirmed even at the 1000 L scale. The results of comparing the virus productivity before and after changing to a medium composition of NCS, hydrolysate, and insulin for each culture scale are shown in FIG. 8. The virus productivity was further increased after changing to the medium, and the equal or higher virus productivity was confirmed even when expanded to a 2000 L culture scale.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are intended to be embraced by the claims.

The invention claimed is:

1. A medium composition for culturing Vero cells, comprising:
   1-7% (v/v) of newborn calf serum (NCS);
   1-6 g/L of hydrolysate; and
   1 mg/L to 4 mg/L of insulin.

2. The medium composition of claim 1, wherein the composition does not contain fetal bovine serum (FBS).

3. The medium composition of claim 1, wherein the hydrolysate is an animal component-free and protein-free hydrolysate.

4. The medium composition of claim 1, wherein the Vero cells are cultured while attached to a microcarrier.

5. The medium composition of claim 1, wherein the medium comprises a MEM medium.

6. A method for culturing Vero cells, comprising culturing the Vero cells in the medium composition of claim 1.

7. The method of claim 6, wherein the culturing is implemented in a scale of 10 mL to 1000 L.

8. A method for producing a virus, comprising:
   infecting Vero cells cultured in the medium composition of claim 1 with a virus; and
   culturing the Vero cells infected with the virus.

9. The method of claim 8, wherein the culturing of the Vero cells infected with the virus is implemented in a scale of 10 mL to 2000 L.

10. The method of claim 6, wherein the composition does not contain fetal bovine serum (FBS).

11. The method of claim 6, wherein the hydrolysate is an animal component-free and protein-free hydrolysate.

12. The method of claim 6, wherein the Vero cells are cultured while attached to a microcarrier.

13. The method of claim 6, wherein the medium comprises a MEM medium.

14. The method of claim 8, wherein the composition does not contain fetal bovine serum (FBS).

15. The method of claim 8, wherein the hydrolysate is an animal component-free and protein-free hydrolysate.

16. The method of claim 8, wherein the Vero cells are cultured while attached to a microcarrier.

17. The method of claim 8 wherein the medium comprises a MEM medium.

* * * * *